US00PP34299P2

(12) United States Plant Patent
van den Hoogen

(10) Patent No.: US PP34,299 P2
(45) Date of Patent: Jun. 7, 2022

(54) ***VERONICA* PLANT NAMED 'ALLVJEWEL'**

(50) Latin Name: ***Veronica longifolia* x *Veronica spicata***
Varietal Denomination: Allvjewel

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 17/546,345

(22) Filed: Dec. 9, 2021

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — C. Anne Whealy

(57) ABSTRACT

A new and distinct cultivar of *Veronica* plant named 'Allvjewel', characterized by its upright plant habit with relatively long stems; dark green-colored leaves; freely flowering habit; dense and relatively long inflorescences with numerous white-colored flowers; and good performance as a garden plant and as a cut flower.

2 Drawing Sheets

Figure 1:
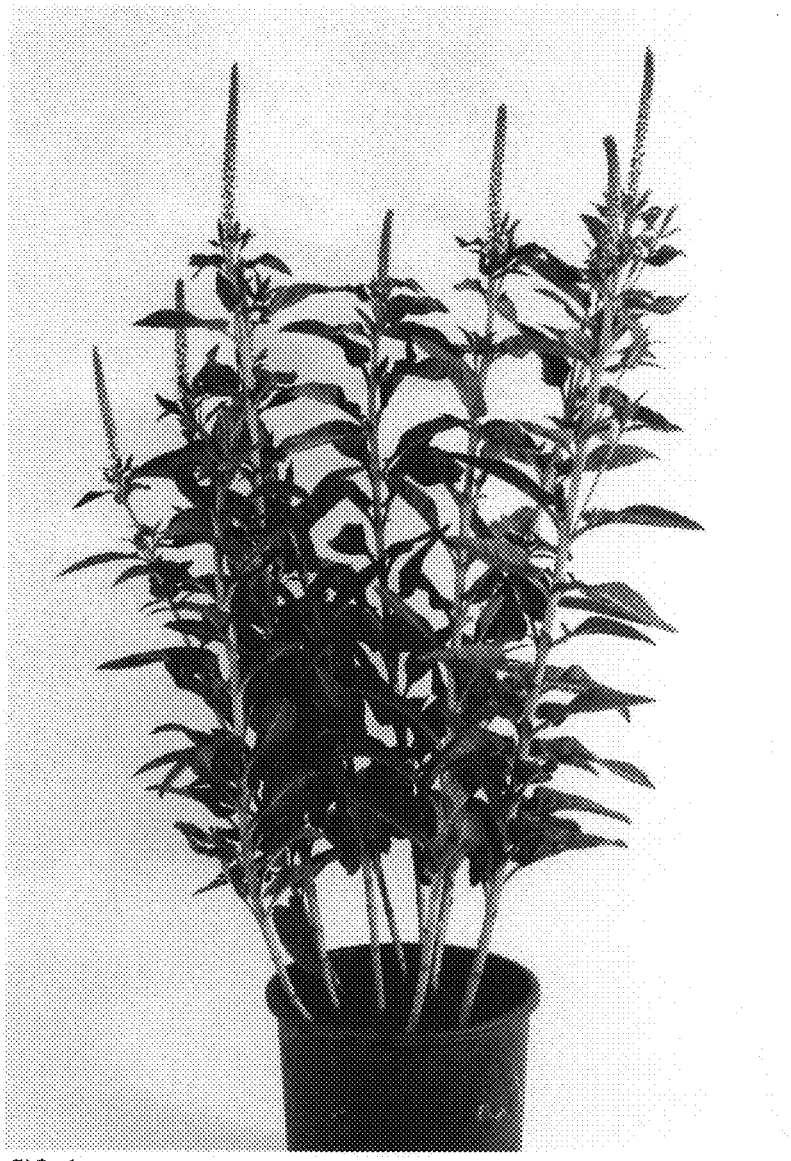

Botanical designation: *Veronica longifolia* x *Veronica spicata.*

Cultivar denomination: 'ALLVJEWEL'.

STATEMENT REGARDING PRIOR DISCLOSURES BY THE INVENTOR/APPLICANT & ASSIGNEE

An European Community Plant Breeder's Rights application for the instant plant was filed by the Assignee, Allplants Holding B.V. of Cuijk, The Netherlands on Aug. 17, 2021, application number 2021/2072 and published on Oct. 15, 2021. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Veronica* plant, botanically known as *Veronica longifolia* x *Veronica spicata*, typically grown as a cut flower and hereinafter referred to by the name 'Allvjewel'.

The new *Veronica* plant is a product of a planned breeding program conducted by the Inventor in Cuijk, The Netherlands. The objective of the breeding program is to create new attractive *Veronica* plants with long inflorescences with attractive flowers.

The new *Veronica* plant originated from an open-pollination in July, 2014 of a proprietary selection of *Veronica*

*longifolia* x *Veronica spicata* identified as code number 1-2013-43-2, not patented, as the female, or seed, parent with an unknown selection of *Veronica longifolia* x *Veronica spicata* as the male, or pollen, parent. The new *Veronica* plant was discovered and selected by the Inventor as a single flowering plant from within the progeny of the stated open-pollination in a controlled nursery environment in Cuijk, The Netherlands in July, 2015.

Asexual reproduction of the new *Veronica* plant by terminal stein cuttings in a controlled environment in Cuijk, The Netherlands, since September, 2015 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvjewel'. These characteristics in combination distinguish 'Allvjewel' as a new and distinct *Veronica* plant:

1. Upright plant habit with relatively long stems.
2. Dark green-colored leaves.
3. Freely flowering habit.
4. Dense and relatively long inflorescences with numerous white-colored flowers.
5. Good performance as a garden plant and as a cut flower.

Plants of the new *Veronica* differ primarily from plants of the female parent selection in the following characteristics:

1. Plants of the new *Veronica* have longer stems than plants of the female parent selection.
2. Plants of the new *Veronica* have longer inflorescences than plants of the female parent selection.

Plants of the new *Veronica* can be compared to plants of *Veronica longifolia* x *Veronica spicata* 'Allluna', not patented. In side-by-side comparisons, plants of the new *Veronica* differ primarily from plants of 'Allluna' in the following characteristics:

1. Plants of the new *Veronica* have longer stems than plants of 'Allluna'.
2. Plants of the new *Veronica* have longer inflorescences than plants of 'Allluna'.
3. Flowers of plants of the new *Veronica* are single-types whereas flowers of plants of 'Allluna' are double-types.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering plant of 'Allvjewel' grown in a container.

Figure 2:
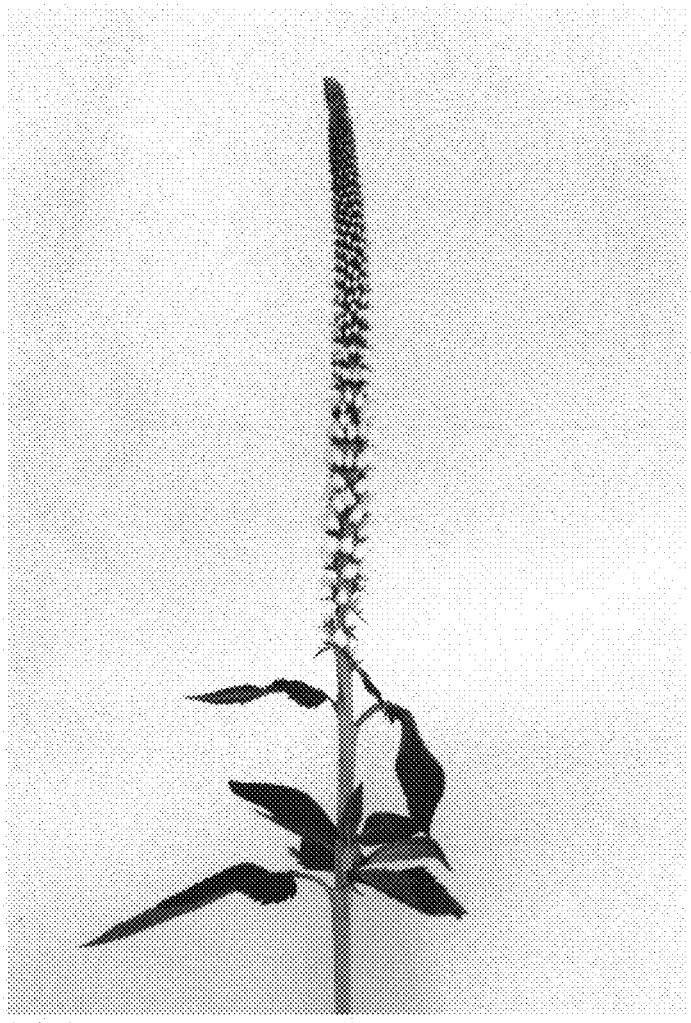
Figure 3:
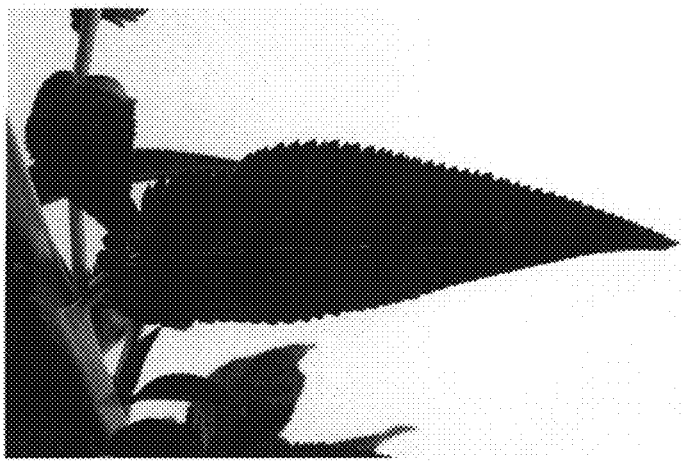

The photographs on the second sheet are close-up views of typical inflorescences (FIG. 2)

and typical leaves (FIG. 3) of 'Allvjewel'.

DETAILED BOTANICAL DESCRIPTION

Plants used for the aforementioned photographs and following description were grown in ground beds and in 20-cm containers during the summer in a outdoor nursery in Timau, Kenya and under cultural practices typical of commercial *Veronica* production. During the production of the plants, day temperatures ranged from 23° C. to 28° C. and night temperatures ranged from 7° C. to 12° C. Plants were six months old when the photographs and the description were taken. In the following description, color references are made to The Royal Horticultural Society Colour Chart, 2015 Edition, except where general terms of ordinary dictionary significance are used.

Botanical classification: *Veronica longifolia* x *Veronica spicata* 'Allvjewel'.

Parentage:

*Female, or seed, parent.*—Proprietary selection of *Veronica longifolia* x *Veronica spicata* identified as code number 1-2013-43-2, not patented.

*Male, or pollen, parent.*—Unknown selection of *Veronica longifolia* x *Veronica spicata*, not patented.

Propagation:

*Type cutting.*—Terminal stein cuttings.

*Time to initiate roots, summer.*—About 10 to 14 days at temperatures ranging from 12° C. to 30° C.

*Time to produce a rooted young plant, summer.*—About 24 to 32 days at temperatures ranging from 12° C. to 30° C.

*Root description.*—Fine, fleshy; typically white in color, actual color of the roots is dependent on substrate composition, water quality, fertilizer type and formulation, substrate temperature and physiological age of roots.

*Rooting habit.*—Freely branching; dense.

Plant description:

*Plant type.*—Herbaceous perennial.

*Plant and growth habit.*—Upright plant habit with relatively long stems and long inflorescences; overall plant shape, narrow inverted triangle; moderately vigorous to vigorous growth habit and moderate growth rate.

*Plant height, soil level to top of foliar plane.*—About 63 cm.

*Plant height, soil level to top of floral plane.*—About 75.5 cm.

*Plant width.*—About 53.6 cm.

*Lateral branch description.*—Branching habit: Freely branching habit with about nine basal stems, each with about two secondary branches; pinching will enhance lateral branching. Length (excluding inflorescence): About 55.4 cm. Diameter: About 8 mm. Internode length: About 3.5 cm. Strength: Strong. Aspect: About 15° from vertical. Texture and luster: Densely pubescent; slightly glossy. Color, developing: Close to 145A. Color, developed: Close to 146D.

Leaf description:

*Arrangement.*—Opposite or in whorls of three, simple.

*Length.*—About 9.5 cm.

*Width.*—About 3.5 cm.

*Shape.*—Lanceolate to narrowly ovate; moderately carinate.

*Apex.*—Narrowly acute.

*Base.*—Truncate.

*Margin.*—Serrate; not lobed.

*Texture and luster, upper surface.*—Moderately to densely pubescent; not rugose; slightly glossy.

*Texture and luster, lower surface.*—Mostly glabrous with exception of midvein which is densely pubescent; not rugose; slightly glossy.

*Venation pattern.*—Pinnate.

*Color.*—Developing leaves, upper surface: Close to 137B. Developing leaves, lower surface: Close to 138A. Fully expanded leaves, upper surface: Darker than a blend of NN137A and 147A; venation, close to 146B. Fully expanded leaves, lower surface: Close to 147B; venation, close to 146D.

*Petioles.*—Length: About 2.1 cm. Diameter: About 3 mm by 5 mm. Strength: Strong. Texture and luster, upper surface: Moderately pubescent; slightly glossy. Texture and luster, lower surface: Sparsely pubescent; slightly glossy. Color, upper surface: Close to 145A; midvein tinged with close to 174A. Color, lower surface: Close to 144B.

Flower description:

*Flower arrangement and shape.*—Single campanulate flowers arranged on dense terminal racemes; flowers face mostly outwardly.

*Flowering habit.*—Freely flowering habit with about 300 flowers developing per inflorescence.

*Fragrance.*—None detected.

*Natural flowering season.*—Long flowering period; plants flower continuously from the summer until the autumn in The Netherlands; plants begin flowering about twelve weeks after planting.

*Flower longevity.*—Inflorescences last about 30 days on the plant and about seven to ten days as a cut flower; flowers not persistent.

*Flower buds.*—Length: About 4 mm. Diameter: About 2.5 mm. Shape: Oblong to broadly ovate. Texture and luster: Smooth, glabrous; matte. Color: Close to NN155D; developing calyx, close to NN137C.

*Inflorescence height* (*length*).—About 15.1 cm.

*Inflorescence diameter.*—About 1.8 cm.

*Flower diameter.*—About 6 mm by 6 mm.

*Flower height.*—About 7 mm.

*Throat diameter.*—About 3.75 mm.

*Tube length.*—About 2.5 mm.

*Tube diameter.*—About 4 mm.

*Petals.*—Quantity and arrangement: Four in a single whorl; upper petal broader than the lateral and lower petals; petals fused about 38.5% of the petal length from the base. Length, all petals: About 6.5 mm. Width, upper petal: About 5 mm. Width, lateral petals: About 1.5 mm. Width, lower petal: About 2 mm. Shape, upper petal: Obovate. Shape, lateral petals: Oblong. Shape, lower petal: Obovate. Apex, all petals: Obtuse. Margin, all petals: Entire; not undulate. Texture and luster, all petals, upper and lower surfaces: Smooth, glabrous; slightly glossy. Texture and luster, throat and tube: Smooth, glabrous; slightly glossy. Color, all petals: When opening, upper and lower surfaces: Close to NN155D. Fully opened, upper and lower surfaces: Close to NN155D; venation, close to NN155D; color does not change with subsequent development. Throat: Close to NN155D; venation, close to NN155D. Tube: Close to NN155D; towards the base, close to 157D; venation, similar to lamina colors.

*Sepals.*—Quantity and arrangement: Four arranged in a single whorl and fused at the base. Length: About 2.5 mm to 3 mm. Width: About 1.25 mm. Shape: Ovate. Apex: Acute. Base: Broadly cuneate, fused. Margin: Entire. Texture and luster, upper and lower surfaces: Smooth, glabrous; matte. Color: When opening, upper and lower surfaces: Close to NN137C. Fully opened, upper and lower surfaces: Close to NN137C and NN137D.

*Peduncles.*—Length: About 14.7 cm. Diameter: About 3 mm. Aspect: Upright; secondary peduncles, about 25° from main peduncle axis. Strength: Strong. Texture and luster: Densely pubescent; slightly glossy. Color: Close to 144A and 144B.

*Pedicels.*—Length: About 1 mm. Diameter: About 0.5 mm. Aspect: About 50° from peduncle axis. Strength: Moderately strong. Texture and luster: Densely pubescent; slightly glossy. Color: Close to 144B.

*Flower bracts.*—Quantity and arrangement: One at the base of each flower. Length: About 5 mm. Width: About 1 mm. Shape: Lanceolate. Apex: Narrowly acute. Base: Attenuate. Margin: Entire. Texture, upper and lower surfaces: Moderately pubescent. Color, upper and lower surfaces: Close to NN137C.

*Reproductive organs.*—Stamens: To date, stamen development has not been observed on plants of the new *Veronica*. Pistils: Quantity per flower: One. Pistil length: About 7 mm. Stigma diameter: About 2 mm. Stigma shape: Club-shaped. Stigma color: Close to 157C to 157D. Style length: About 6.5 mm. Style color: Close to NN155D. Ovary color: Close to a blend of 143C and 144C.

*Seeds and fruits.*—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −29° C. to about 35° C. and to be suitable for USDA Hardiness Zones 4 through 9.

It is claimed:

1. A new and distinct *Veronica* plant named 'Allvjewel' as illustrated and described.

* * * * *